(12) United States Patent
Sonderman

(10) Patent No.: US 6,818,561 B1
(45) Date of Patent: Nov. 16, 2004

(54) CONTROL METHODOLOGY USING OPTICAL EMISSION SPECTROSCOPY DERIVED DATA, SYSTEM FOR PERFORMING SAME

(75) Inventor: Thomas J. Sonderman, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 238 days.

(21) Appl. No.: 10/208,542

(22) Filed: Jul. 30, 2002

(51) Int. Cl.$^7$ .............................................. H01L 21/302
(52) U.S. Cl. ............................ 438/706; 438/70; 438/7; 438/710; 216/60
(58) Field of Search .................................. 438/706, 710, 438/712, 720, 7, 9, 10, 14; 216/58, 60; 210/67

(56) References Cited

U.S. PATENT DOCUMENTS 5,653,894 A * 8/1997 Ibbotson et al. .............. 216/59
6,368,975 B1 * 4/2002 Balasubramhanya et al. .......................... 438/706

* cited by examiner

Primary Examiner—Lan Vinh
(74) Attorney, Agent, or Firm—Williams, Morgan & Amerson, P.C.

(57) ABSTRACT

The present invention is generally directed to various control methodologies using optical emission spectroscopy derived data, and a system for performing same. In one illustrative embodiment, the method comprises performing an etching process within an etch tool to define at least one feature above a semiconducting substrate, obtaining optical emission spectroscopy data for the etching process, and controlling at least one parameter of the etching process based upon a comparison of the obtained optical emission spectroscopy data and target optical emission spectroscopy data associated with at least one of a target profile and a target critical dimension for the at least one feature. In one illustrative embodiment, the system is comprised of an etch tool adapted to perform an etch process to define at least one feature, an optical emission spectroscopy sensor operatively coupled to the etch tool, and a controller for controlling at least one parameter of the etching process performed in the etch tool based upon a comparison between optical emission spectroscopy data obtained from the optical emission spectroscopy sensor and target optical emission spectroscopy data associated with at least one of a target profile and a target critical dimension for the at least one feature.

25 Claims, 3 Drawing Sheets

CONTROL METHODOLOGY USING OPTICAL EMISSION SPECTROSCOPY DERIVED DATA, SYSTEM FOR PERFORMING SAME

BACKGROUND OF THE INVENTION

1. Field of the Invention

The present invention is generally related to the field of semiconductor manufacturing and, more particularly, to various control methodologies using optical emission spectroscopy derived data, and a system for performing same.

2. Description of the Related Art

There is a constant drive within the semiconductor industry to increase the quality, reliability and throughput of integrated circuit devices, e.g., microprocessors, memory devices, and the like. This drive is fueled by consumer demands for higher quality computers and electronic devices that operate more reliably. These demands have resulted in a continual improvement in the manufacture of semiconductor devices, e.g., transistors, as well as in the manufacture of integrated circuit devices incorporating such transistors. Additionally, reducing the defects in the manufacture of the components of a typical transistor also lowers the overall cost per transistor as well as the cost of integrated circuit devices incorporating such transistors.

As device dimensions have continued to decrease, the ability to precisely form very small features to their desired dimension has become more important. Variations in the physical dimensions of such features can adversely impact device performance and reduce product yields. For example, the critical dimension and profile of gate electrode structures of transistors is one area where a very high degree of precision is desired. Absent precise control, adverse consequences may follow. For example, if the critical dimension of the gate electrode is greater than the target or design critical dimension, the transistor may not operate as fast as desired by the product design requirements. Conversely, if the critical dimension of the gate electrode structure is less than the target value, off-state leakage currents may be higher than desired. This situation is particularly problematic for integrated circuit devices intended for mobile telecommunication applications and those intended for mobile computing devices.

Etching processes are frequently employed in semiconductor manufacturing to define a variety of different types of features, such as gate electrode structures, conductive metal lines, openings in insulating layers, trenches in a semiconducting substrate, sidewall spacers, etc. Such etching processes, be they anisotropic or isotropic in nature, are very complex processes that involve a vast variety of interrelated variables, such as gas flow rates, temperature, pressure, power, and the characteristics of the plasma generated in some of the processes. Such complexities make it difficult to control etching processes such that the resulting features exhibit the desired physical dimensions and/or profile.

The present invention is directed to overcoming, or at least reducing the effects of, one or more of the problems set forth above.

SUMMARY OF THE INVENTION

The present invention is generally directed to various control methodologies using optical emission spectroscopy derived data, and a system for performing same. In one illustrative embodiment, the method comprises performing an etching process within an etch tool to define at least one feature above a semiconducting substrate, obtaining optical emission spectroscopy data for the etching process, and controlling at least one parameter of the etching process based upon a comparison of the obtained optical emission spectroscopy data and target optical emission spectroscopy data associated with at least one of a target profile and a target critical dimension for the at least one feature. In further embodiments, the controller acts to control one or more parameters of the etching process such that a metric for the obtained optical spectroscopy data is maintained within a preselected range of a metric for the target optical emission spectroscopy data. In even further embodiments, the metric for the obtained optical spectroscopy data is maintained below a preselected level or limit of a metric for the target optical emission spectroscopy data.

In one illustrative embodiment, the system is comprised of an etch tool adapted to perform an etch process to define at least one feature, an optical emission spectroscopy sensor operatively coupled to the etch tool, and a controller for controlling at least one parameter of the etching process performed in the etch tool based upon a comparison between optical emission spectroscopy data obtained from the optical emission spectroscopy sensor and target optical emission spectroscopy data associated with at least one of a target profile and a target critical dimension for the at least one feature. In further embodiments, the controller acts to control one or more parameters of the etching process such that a metric for the obtained optical spectroscopy data is maintained within a preselected range of a metric for the target optical emission spectroscopy data. In even further embodiments, the metric for the obtained optical spectroscopy data is maintained below a preselected level or limit of a metric for the target optical emission spectroscopy data.

BRIEF DESCRIPTION OF THE DRAWINGS

The invention may be understood by reference to the following description taken in conjunction with the accompanying drawings, in which like reference numerals identify like elements, and in which.

Figure 1A:
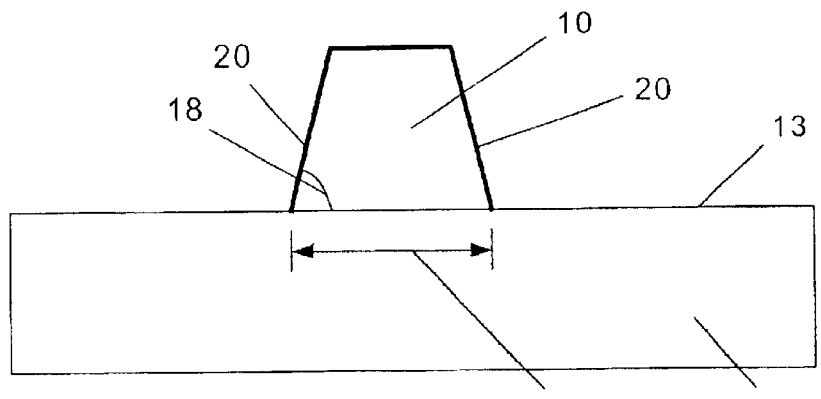
FIGS. 1A–1C depict an illustrative feature that has physical dimensions that vary from a target dimension.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various features of a semiconductor device are depicted in the drawings as having very precise, sharp configurations and profiles, those skilled in the art recognize that, in reality, these features are not as precise as indicated in the drawings. Additionally, the relative sizes of the various features depicted in the drawings may be exaggerated or reduced as compared to the size of those features or regions on fabricated devices. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In general, the present invention is directed to various control methodologies using optical emission spectroscopy derived data, and a system for performing same. As will be readily apparent to those skilled in the art upon a complete reading of the present application, the present methods are applicable to a variety of technologies, e.g., NMOS, PMOS, CMOS, SOI, etc., and the methods disclosed herein may be used in the formation of a variety of different types of integrated circuit devices, including, but not limited to, logic devices, memory devices, etc.

The present invention is generally directed to various control methodologies that may be employed in the context of forming a variety of different types of features during the course of manufacturing an integrated circuit product. For example, the present invention may be employed in the context of forming trench-type features or island-type features in an integrated circuit device. Even more specifically, the present invention may be employed in the context of forming features such as trenches in a semiconducting substrate, gate electrode structures, conductive metal lines, openings in layers of insulating material, etc. Thus, as will be appreciated by those skilled in the art after a complete reading of the present application, the present invention should not be considered as limited to any particular type of feature unless such feature type is specifically set forth in the appended claims.

Figure 1B:
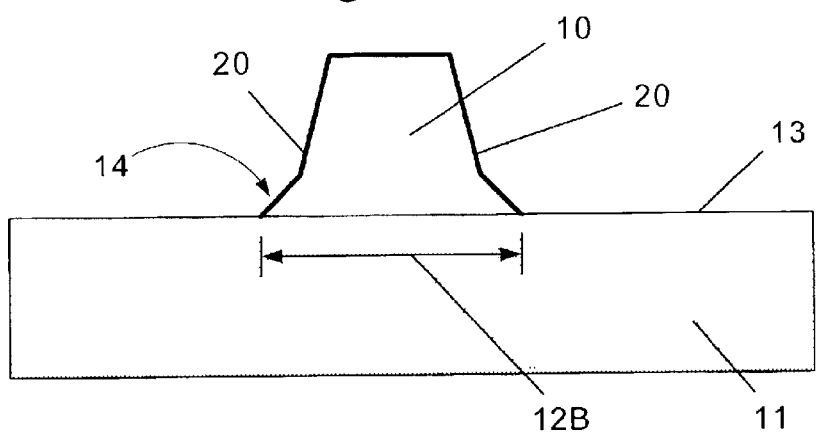
Figure 1C:
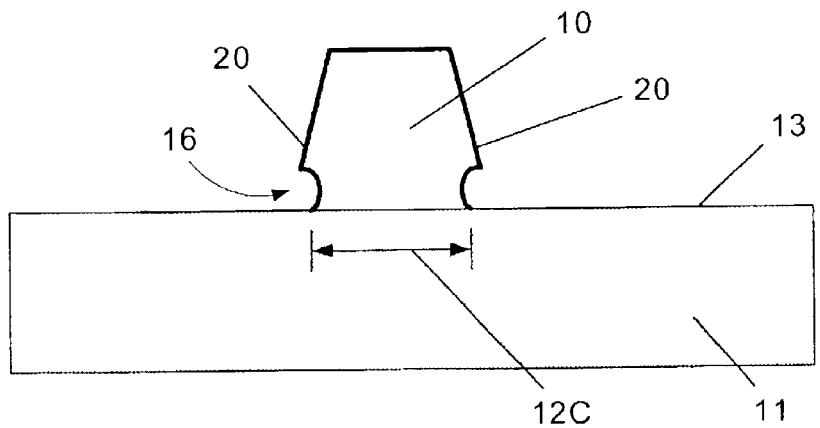

As set forth in the background section of this application, the variations in the physical dimensions and/or profile of a feature may adversely impact the performance of an integrated circuit device and/or reduce product yields. FIGS. 1A–1C are provided to graphically depict an illustrative feature 10 wherein, due to a variety of factors, the critical dimension and/or cross-sectional profile of the features depicted in FIGS. 1B and 1C vary from the target critical dimension and/or profile of the feature 10 depicted in FIG. 1A. The feature 10 depicted in FIGS. 1A–1C is intended to be representative in nature, as the present invention may be employed in the context of forming a variety of different types of features. For purposes of explanation only, the feature 10 may be considered to be a gate electrode structure. The feature 10 depicted in FIG. 1A has a critical dimension 12 and a plurality of sidewalls 20 that are positioned at an angle 18 relative to the surface 13 of the substrate 11.

The feature 10B depicted in FIG. 1B exhibits an undesirable amount of footing or flaring 14 which tends to make the critical dimension 12B greater than the target critical dimension 12 in FIG. 1A. The feature 10C depicted in FIG. 1C exhibits undercutting 16 which tends to make the critical dimension 12C less than the target critical dimension 12 depicted in FIG. 1A. The flaring and undercutting depicted in FIGS. 1B and 1C may be due to a variety of factors, such as defective etching procedures, defective etching materials, defective etch equipment, poor maintenance procedures and routines, etc. Of course, other types of variations in the profile of the feature 10 are possible, such as variations in sidewall angle 18 or the roughness of the sidewall surface 20. As should be clear from the foregoing, the feature 10 depicted in FIGS. 1A–1C is provided by way of example only, and the specific deviations in the profile and/or critical dimension of the feature 10 are discussed only by way of example.

As described earlier, many features formed in semiconductor manufacturing operations are formed by performing a variety of known etching processes to define the features. Such etching processes include, but are not limited to, plasma etching processes, etc., that may be anisotropic or isotropic in nature. Thus, it should be understood that the present invention may be employed with any of a variety of different types of etching tools and processes.

Figure 2:
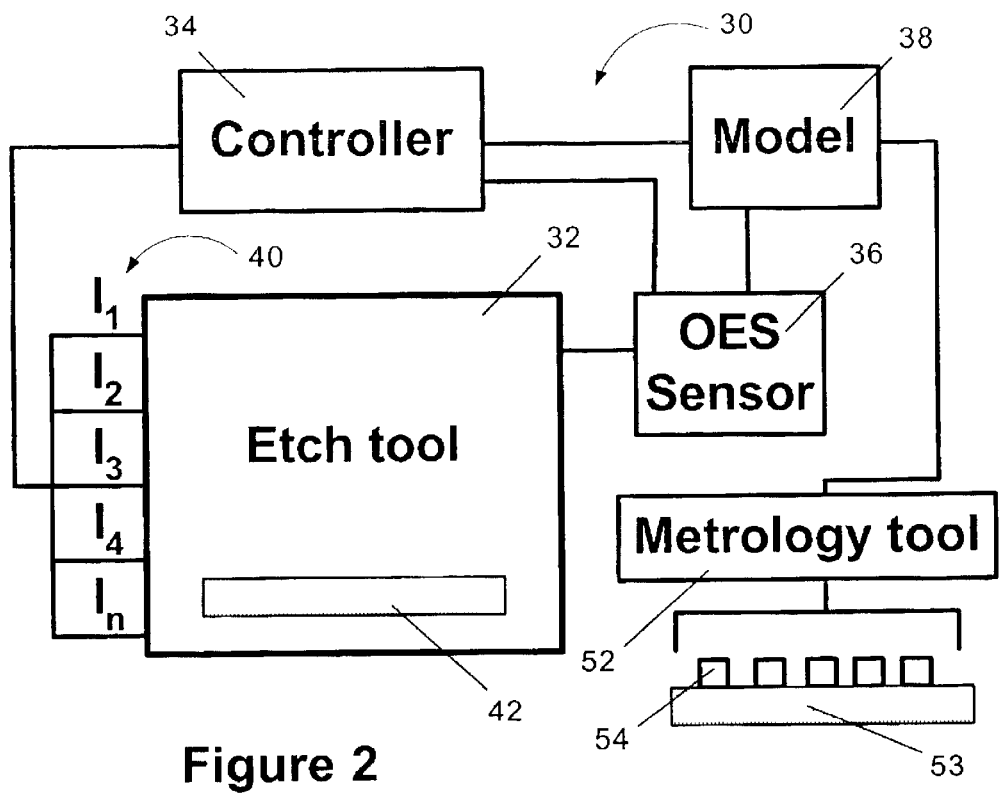
FIG. 2 is a block diagram, schematic depiction of a system in accordance with one illustrative embodiment of the present invention.

FIG. 2 depicts an illustrative system 30 that may be employed with the present invention. In general, in one embodiment, the system 30 is comprised of an etch tool 32, a controller 34, an optical emission spectrometry (OES) sensor 36 and a model 38. The controller 34 is adapted to control a plurality of input parameters ($I_{1-In}$), indicated generally by the arrow 40, to control one or more aspects of the etching process performed in the etch tool 32. Such parameters may include, but should not be considered as limited to, one or more gas flow rates, temperature, pressure, power supplied to a plasma generator, the positioning of the schematically depicted wafer 42 within the etch tool 32, etc. The controller 34 may be resident on the etch tool 32, it may be a stand-alone computer, or it may be part of a factory-wide computer system that is used to control the various processes within a semiconductor manufacturing plant.

The OES sensor 36 may be any of a variety of known optical emission spectroscopy tools or sensors, such as, for example, the "ProPak" real time, full spectrum plasma process monitoring tool sold by Peak Sensor Systems. In some cases, such OES equipment is used to endpoint or stop an etching process performed in the etch tool 32 when an analysis of the offgases of the etching process indicate that the etching process is complete.

The controller 34 may use the control model 38 in performing at least some of its activities. The model 38 may correlate optical emission spectroscopy data with a desired or target physical dimension of a feature such as a critical dimension of the feature or a profile of the feature. The control model 38 may be developed empirically using any of a variety of known linear or non-linear techniques. The model 38 may be a relatively simple equation-based model (e.g., linear, exponential, weighted average, etc.) or a more complex model, such as a neural network model, principal component analysis (PCA) model, or a projection to latent structures (PLS) model. The specific implementation of the model 38 may vary depending upon the modeling technique selected. The model 38 may be generated by the controller 34 or, alternatively, it may be generated by a different processing resource (not shown) and stored on the controller 34 or another data storage resource (not shown) after being developed. The controller 34 may access the model 38 at any desired time.

A metrology tool 52 may be used to update or create the model 38. The metrology tool 52 may be any type of tool capable of measuring a desired physical characteristic of the features formed by the etch process performed in the etch tool 32. An illustrative substrate 53 having a plurality of schematically-depicted manufactured features 54 formed thereon is shown in FIG. 2. The metrology tool 52 may be, for example, a scatterometry tool or a scanning electron microscope (SEM). Other types of metrology tools may be used depending upon the characteristic of the feature that is being examined. Simply put, the model 38 may be updated or trained based upon the metrology data obtained by the metrology tool 52 for various manufactured features 54 and optical emission spectroscopy data obtained from the OES sensor 36 during the etch processes used to form the manufactured features. The model 38 may be used to determine the OES data associated with the manufactured features 54 that have a desired or acceptable physical dimension or profile. Through this process the model may associate one or more characteristics of the OES data used to form the manufactured features 54 with a target physical dimension or profile of the feature. As a result, target optical emission spectroscopy data may be determined. This target optical emission spectroscopy data may be associated with a desirable or target physical aspect of the feature, e.g., a critical dimension, a profile, etc.

In the illustrated embodiments, the controller 34 is a computer programmed with software to implement the functions described herein. Moreover, the functions described for the controller 34 may be performed by one or more controllers spread through the system. For example, the controller 34 may be a fab level controller that is used to control processing operations throughout all or a portion of a semiconductor manufacturing facility. Alternatively, the controller 34 may be a lower level computer that controls only portions or cells of the manufacturing facility. Moreover, the controller 34 may be a stand-alone device, or it may reside on the etch tool 32 or elsewhere within the system. However, as will be appreciated by those of ordinary skill in the art, a hardware controller (not shown) designed to implement the particular functions may also be used.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the controller 34, as described, is the Catalyst system offered by KLA Tencor, Inc. The Catalyst system uses Semiconductor Equipment and Materials International (SEMI) Computer Integrated Manufacturing (CIM) Framework compliant system technologies, and is based on the Advanced Process Control (APC) Framework. CIM (SEMI E81-0699-Provisional Specification for CIM Framework Domain Architecture) and APC (SEMI E93-0999-Provisional Specification for CIM Framework Advanced Process Control Component) specifications are publicly available from SEMI.

Figure 3:
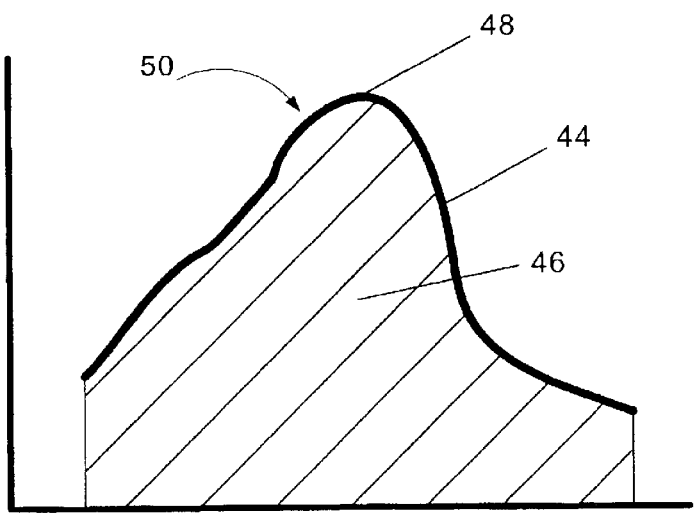
FIG. 3 is an illustrative graphical depiction of OES data that may be employed in the context of the present invention.

According to the present invention, the data derived from the OES sensor 36 is used to establish a characteristic signature or fingerprint for the etch process performed in the etch tool 32. A metric may be established for this characteristic signature or fingerprint. For example, FIG. 3 is a simplified graphic depiction of a potential signature or fingerprint of the etching process performed in the etch tool 32. The curve 44 is a graphical representation of one or more items of data provided by the OES sensor 36. For example, such data may include the quantity of one or more elements in the offgases of the etching process. The particular elements will vary depending upon the particular application.

As stated previously, a metric may be created for the data obtained from the OES sensor 36. For example, the area 46 under the curve 44 may be one such metric. Other possible metrics include, by way of example, the height 48 of the curve 44, the slope of the curve 44 in the region 50 right before the peak height 48, the value of one or more material species in the offgas, etc. Thus, the metric established for the OES derived data may be varied depending upon the application.

Once one or more metrics are established for the OES derived data, the metric may be correlated with a target profile or critical dimension of the features to be formed by performing an etching process in the etch tool 32. More particularly, the model 38 may be created to correlate such OES data with a desired or target profile for a feature. As shown in FIG. 3, the metrology tool 52 may be employed to train and/or update the model 38 based upon metrology data obtained for manufactured features 54 that are schematically depicted above a wafer 53 that has previously been processed. More specifically, the metrology tool 54 may be used to measure or determine the critical dimension and/or profile of the manufactured features 54. The model 38 may then correlate the OES data for the etch process used to form the manufactured features 54 with the metrology data, e.g., profile, critical dimension, for the features 54.

Based upon the metrology data obtained by the metrology tool 52, features that match or closely approximate the target profile or critical dimension for the features may be readily identified. The OES data, e.g., graph 44, associated with such acceptable features may then be treated as the target for OES data generated during the etch process performed in the etch tool 32. For example, if the metric for OES derived data is the area 46 under the curve 44, then the controller 34 may adjust one or more parameters 40 of the etch process to insure that the OES data generated during the etch process does not exceed this area, or at least falls within a certain predetermined allowable range of this target value.

Thus, through use of the present invention, the OES derived data may be used as a virtual sensor to control the etching processes performed in the etch tool 32. As long as the etch tool 32 is producing OES data where the selected metric for the data, e.g., area under the curve, height, falls within an acceptable range of this selected metric, then the resulting feature should exhibit the desired profile and/or critical dimension.

Figure 4:
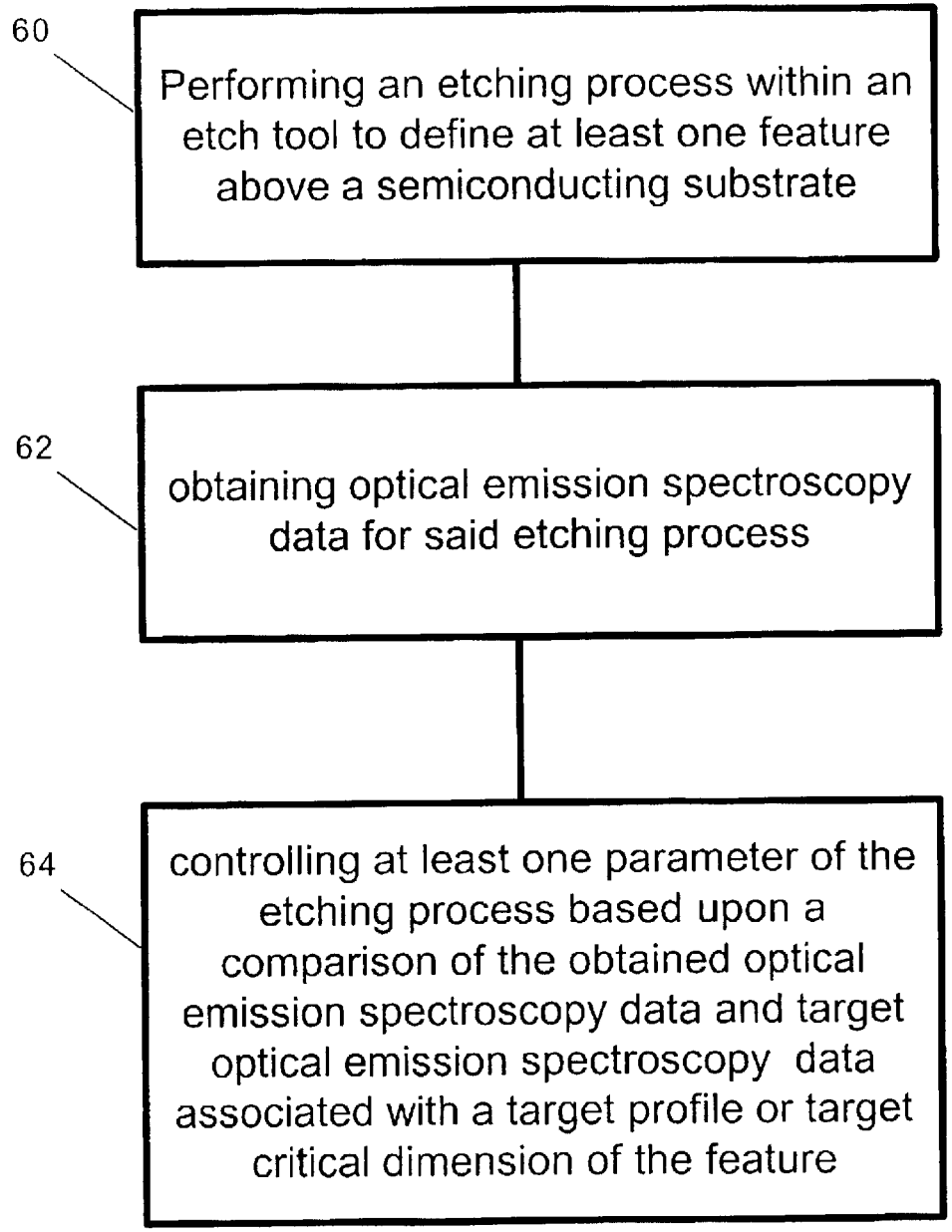
FIG. 4 is a flowchart depiction of one illustrative embodiment of the present invention.

FIG. 4 depicts one illustrative embodiment of the present invention in flowchart form. As shown therein, in one embodiment, a method according to the present invention comprises performing an etching process within an etch tool to define at least one feature above a semiconducting substrate, as indicated at block 60, and obtaining optical emission spectroscopy data for the etching process, as set forth at block 62. The method further comprises controlling at least one parameter of the etching process based upon a comparison of the obtained optical emission spectroscopy data associated with at least one of a target profile and a target critical dimension for the feature. In further embodiments, the controller acts to control one or more parameters of the etching process such that a metric for the obtained optical spectroscopy data is maintained within a preselected range of a metric for the target optical emission spectroscopy data. In even further embodiments, the etch process is controlled such that the metric for the obtained optical spectroscopy data is maintained below a preselected level or limit of a metric for the target optical emission spectroscopy data.

The present invention is also directed to a system for performing the various methods disclosed herein. In one illustrative embodiment, the system is comprised of an etch tool adapted to perform an etch process to define at least one feature above a semiconducting substrate, an optical emission spectroscopy sensor operatively coupled to the etch tool, and a controller for controlling at least one parameter of the etching process performed in the etch tool based upon a comparison between optical emission spectroscopy data obtained from the optical emission spectroscopy sensor and target optical emission spectroscopy data associated with at least one of a target profile and a target critical dimension for the at least one feature.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:
   performing an etching process within an etch tool to define at least one feature above a semiconducting substrate;
   obtaining optical emission spectroscopy data for said etching process; and
   controlling at least one parameter of said etching process based upon a comparison of said obtained optical emission spectroscopy data and target optical emission spectroscopy data associated with at least one of a target profile and a target critical dimension for said at least one feature.

2. The method of claim 1, wherein performing an etching process comprises performing at least one of an anisotropic and an isotropic etching process.

3. The method of claim 1, wherein obtaining optical emission spectroscopy data for said etching process comprises obtaining optical emission spectroscopy data for said etching process by use of an optical spectroscopy sensor operatively coupled to said etch tool.

4. The method of claim 1, wherein controlling at least one parameter comprises controlling at least one of a temperature, a pressure, a gas flow rate, a position of said substrate, and a power supplied to said etch tool.

5. The method of claim 1, wherein said feature is comprised of at least one of a trench-type feature and an island-type feature.

6. The method of claim 1, wherein said comparison between said obtained optical emission spectroscopy data and said target optical emission spectroscopy data is performed by a controller.

7. The method of claim 1, wherein said controlling of at least one parameter of said etching process comprises controlling at least one parameter of said etching process such that a metric for said obtained optical emission spectroscopy data is maintained within a preselected range of a metric for said target optical emission spectroscopy.

8. The method of claim 1, wherein said controlling of at least one parameter of said etching process comprises controlling at least one parameter of said etching process such that a metric for said obtained optical emission spectroscopy data is less than a preselected limit for a metric for said target optical emission spectroscopy.

9. A method, comprising:
   performing an etching process within an etch tool to define at least one feature above a semiconducting substrate;
   obtaining optical emission spectroscopy data for said etching process; and
   controlling at least one parameter of said etching process based upon a comparison of a metric value for said obtained optical emission spectroscopy data and a metric value for a target optical emission spectroscopy data associated with at least one of a target profile and a target critical dimension for said at least one feature.

10. The method of claim 9, wherein performing an etching process comprises performing at least one of an anisotropic and an isotropic etching process.

11. The method of claim 9, wherein obtaining optical emission spectroscopy data for said etching process comprises obtaining optical emission spectroscopy data for said etching process by use of an optical spectroscopy sensor coupled to said etch tool.

12. The method of claim 9, wherein controlling at least one parameter comprises controlling at least one of a temperature, a pressure, a gas flow rate, a position of said substrate, and a power supplied to said etch tool.

13. The method of claim 9, wherein said feature is comprised of at least one of a trench-type feature and an island-type feature.

14. The method of claim 9, wherein said comparison between said metric value for said obtained optical emission spectroscopy data and said metric value for said target optical emission spectroscopy data is performed by a controller.

15. The method of claim 9, wherein said controlling of at least one parameter of said etching process comprises controlling at least one parameter of said etching process such that the metric value for said obtained optical emission spectroscopy data is maintained within a preselected range of said metric value for said target optical emission spectroscopy data.

16. The method of claim 9, wherein said controlling of at least one parameter of said etching process comprises controlling at least one parameter of said etching process such that the metric value for said obtained optical emission spectroscopy data is less than a preselected limit for said metric value for said target optical emission spectroscopy data.

17. The method of claim 9, wherein said metric value for said obtained optical emission spectroscopy data and said metric for said target optical emission spectroscopy data is comprised of at least one of a value of a material species in an offgas of said etching process, a peak value of a material in an offgas of said etching process, an area under a curve that is representative of an analysis of an offgas of said etching process, and a slope of a portion of a graph that is representative of an analysis of an offgas of said etching process.

18. A method, comprising:
    performing an etching process within an etch tool to define at least one feature above a semiconducting substrate;
    obtaining optical emission spectroscopy data for said etching process; and
    controlling at least one parameter of said etching process based upon a comparison of a metric value for said obtained optical emission spectroscopy data and a metric value for a target optical emission spectroscopy data associated with at least one of a target profile and a target critical dimension for said at least one feature, wherein said metric value for said obtained optical spectroscopy data is maintained within a preselected range of said metric for said target optical emission spectroscopy data associated with said at least one of said target profile and said target critical dimension for said at least one feature.

19. The method of claim 18, wherein performing an etching process comprises performing at least one of an anisotropic and an isotropic etching process.

20. The method of claim 18, wherein obtaining optical emission spectroscopy data for said etching process comprises obtaining optical emission spectroscopy data for said etching process by use of an optical spectroscopy sensor coupled to said etch tool.

21. The method of claim 18, wherein controlling at least one parameter comprises controlling at least one of a temperature, a pressure, a gas flow rate, a position of said substrate, and a power supplied to said etch tool.

22. The method of claim 18, wherein said feature is comprised of at least one of a trench-type feature and an island-type feature.

23. The method of claim 18, wherein said comparison between said obtained optical emission spectroscopy data and said target optical emission spectroscopy data is performed by a controller.

24. The method of claim 18, wherein said controlling of at least one parameter of said etching process further comprises controlling at least one parameter of said etching process such that the metric value for said obtained optical emission spectroscopy data is less than a preselected limit for said metric value for said target optical emission spectroscopy data.

25. The method of claim 18, wherein said metric value for said obtained optical emission spectroscopy data and said metric for said target optical emission spectroscopy data is comprised of at least one of a value of a material species in an offgas of said etching process, a peak value of a material in an offgas of said etching process, an area under a curve that is representative of an analysis of an offgas of said etching process, and a slope of a graph that is representative of an analysis of an offgas of said etching process.

* * * * *